US012663417B2

(12) United States Patent
Armbruster et al.

(10) Patent No.: US 12,663,417 B2
(45) Date of Patent: Jun. 23, 2026

(54) RAPID TEST FOR DIAGNOSIS OF BACTERIAL INFECTIONS IN NEONATES

(71) Applicant: Immundiagnostik AG, Bensheim (DE)

(72) Inventors: Franz-Paul Armbruster, Bobenheim-Roxheim (DE); Brigitte Koenig, Magdeburg (DE)

(73) Assignee: IMMUNDIAGNOSTIK AG, Bensheim (DE)

( * ) Notice: Subject to any disclaimer, the term of this patent is extended or adjusted under 35 U.S.C. 154(b) by 946 days.

(21) Appl. No.: 17/430,767

(22) PCT Filed: Feb. 17, 2020

(86) PCT No.: PCT/EP2020/054117
§ 371 (c)(1),
(2) Date: Aug. 13, 2021

(87) PCT Pub. No.: WO2020/165456
PCT Pub. Date: Aug. 20, 2020

(65) Prior Publication Data
US 2022/0163525 A1     May 26, 2022

(30) Foreign Application Priority Data
Feb. 15, 2019     (DE) ..................... 10 2019 103 940.1

(51) Int. Cl.
| | |
|---|---|
| *G01N 33/543* | (2006.01) |
| *A01N 1/124* | (2025.01) |
| *G01N 1/38* | (2006.01) |
| *G01N 33/569* | (2006.01) |

(52) U.S. Cl.
CPC ....... *G01N 33/54388* (2021.08); *A01N 1/124* (2025.01); *G01N 1/38* (2013.01); *G01N 33/56911* (2013.01); *G01N 2333/4727* (2013.01); *G01N 2800/26* (2013.01)

(58) Field of Classification Search
CPC .............. G01N 33/54388; G01N 1/38; G01N 33/56911; G01N 2333/4727; G01N 2800/26; A01N 1/0215
See application file for complete search history.

(56) References Cited

U.S. PATENT DOCUMENTS

| | | | |
|---|---|---|---|
| 6,787,660 | B1 | 9/2004 | Armbruster et al. |
| 7,851,163 | B2 | 12/2010 | Armbruster et al. |
| 7,943,579 | B2 | 5/2011 | Armbruster et al. |
| 7,964,363 | B2 | 6/2011 | Armbruster et al. |
| 8,133,694 | B2 | 3/2012 | Armbruster et al. |
| 9,140,711 | B2 | 9/2015 | Armbruster et al. |
| 9,823,258 | B2 | 11/2017 | Armbruster et al. |
| 10,253,092 | B2 | 4/2019 | Armbruster et al. |
| 10,317,419 | B2 | 6/2019 | Armbruster et al. |
| 10,613,101 | B2 | 4/2020 | Armbruster et al. |
| 10,947,301 | B2 | 3/2021 | Armbruster et al. |
| 11,085,922 | B2 | 8/2021 | Armbruster et al. |
| 2005/0054016 | A1 | 3/2005 | Armbruster et al. |
| 2012/0107407 | A1 | 5/2012 | Armbruster et al. |

FOREIGN PATENT DOCUMENTS

| | | |
|---|---|---|
| WO | 2013132347 A2 | 9/2013 |

OTHER PUBLICATIONS

Yetisen, Ali Kemal et al. "Paper-based microfluidic point-of-care diagnostic devices." Lab on a chip vol. 13,12 (2013): 2210-51. doi: 10.1039/c3lc50169h (Year: 2013).*
Vecchione, J.J., et al., "Circulation and function of human platelets isolated from units of CPDA-1, CPDA-2, and CPDA-3 anticoagulated blood and frozen with DMSO". Transfusion, 22: 206-209 (1982). https://doi.org/10.1046/j.1537-2995.198 (Year: 1982).*
Polat, Gizem et al. "Sepsis and Septic Shock: Current Treatment Strategies and New Approaches." The Eurasian journal of medicine vol. 49,1 (2017): 53-58. doi:10.5152/eurasianjmed.2017.17062 (Year: 2017).*
del Pino, Isabel García et al. "Citric/citrate buffer: an effective antiglycolytic agent." Clinical chemistry and laboratory medicine vol. 51,10 (2013): 1943-9. doi:10.1515/cclm-2012-0735 (Year: 2013).*
Beutler, E, and C West. "The storage of hard-packed red blood cells in citrate-phosphate-dextrose (CPD) and CPD-adenine (CPDA-1)." Blood vol. 54,1 (1979): 280-4. (Year: 1979).*
Terrin et al., "Serum calprotectin: an antimicrobial peptide as a new marker for the diagnosis of sepsis in very low birth weight newborns." Clinical & developmental immunology vol. 2011 (2011):291085. doi:10.1155/2011/291085. (Year: 2011).*
Medkova et al., "Multifarious Diagnostic Possibilities of the S100 Protein Family: Predominantly in Pediatrics and Neonatology," 14 World J. Pediatrics 315 (2018).
A. Nydegger, "Calprotectin in der Padiatrie," 27 Padiatrische Gastroenterologie, Hepatologie und Ernahrung 18 (2016).
Buhimschi et al., "Proteomic But Not Enzyme-linked Immunosorbent Assay Technology Detects Amniotic Fluid Monomeric Calgranulins From Their Complexed Calprotectin Form", 12 Clin. Diagnostic Lab. Immunology 837 (2005).

* cited by examiner

*Primary Examiner* — Gregory S Emch
*Assistant Examiner* — Mckenzie A Dunn
(74) *Attorney, Agent, or Firm* — Birch, Stewart, Kolasch & Birch, LLP

(57) ABSTRACT

The disclosure relates to a point-of-care test device for diagnosis and detection of bacterial infections and hidden septic processes in samples of bodily fluids of premature and newborns comprising a quantitative or semi-quantitative lateral flow immunoassay unit adapted for parallel detection of proteins of the S100 family and for several detection of increased amounts of S100A12 and calprotectin in blood, serum, plasma, and saliva.

12 Claims, 3 Drawing Sheets

RAPID TEST FOR DIAGNOSIS OF BACTERIAL INFECTIONS IN NEONATES

FIELD OF THE INVENTION

The present disclosure relates to the field of test devices for quantitative or semi-quantitative determination of an analyte in a sample, and in particular to a point-of-care test in the field of medical diagnostics of bacterial infections and/or sepsis.

BACKGROUND OF THE INVENTION

Up to 10% of neonates and about 5% of infants up 3 months are subject to bacterial infections. Bacterial infections and sepsis are particularly dangerous in preterm infants where sepsis leads to death in about 10 to 16% of the cases. Among the survivors, CNS damage and/or long-term mental retardation are frequent (Niehues T, Das *fiebernde Kind: Diagnostisches Vorgehen and Behandlung*, Deutsches Ärzteblatt 2013, 110:45). The symptoms of a bacterial infection in prematures and newborns are non-specific and include skin alterations as well as respiratory or circulation disorders, lethargy, drinking weakness, etc. Fever may appear in cases of bacterial infections of the intestines, respiratory tract and urinary tract. However, fever reactions may also be caused by viruses, toxins and/or non-infectious inflammations. Fever is therefore no reliable sign of a bacterial infection and, additionally, systemic infections can occur in preterm and newly born infants without the development of fever. This represents a major challenge for nurses and clinicians to discern whether a prematurely or newly born patients is suffering from a bacterial infection and requires treatment with antibiotics (*AWMF S2-Leitlinie Neonatologie*).

In clinical diagnostics lateral flowthrough assays are being developed for rapid bedside stratification of bloodstream bacterial infections in critically ill patients. The flowthrough or lateral-flow binding assay takes place on the membrane of a thin-layer chromatography so that the speed of the flowthrough separation and the specificity of an immunoassay can be used. A class of lateral flow assays relates to sandwich-type assays which require a mixing of a test sample with antibodies or immunoreactants against the analyte. The immunoreactants are in the mobile phase and lead to a label (dyed latex, gold nanoparticles) or probe with an enzyme catalyzing a color reaction. Lateral flow tests are usually in the form of a dipstick or configured as a drop-on cassette. When the complex of analyte and labeled immunoreactant reaches the zone of immobilized anti-analyte antibodies on the chromatographic membrane, binding occurs and the label becomes concentrated at the zone. A concentrated label indicates a presence of analyte in the probe, and the intensity of the colored zone can be used to quantify the amount of analyte therein. The analyte may be any biomolecule or protein, a nucleic acid or a PCR product (cf. EP029130194 B2). In some embodiments, haptens and haptenylated agents have been used to indirectly bind members of a specific binding pair to a carrier membrane. A well known example of a haptenylated non-immunological binding pair is the biotin/avidin or biotin/streptavidin-system (cf. U.S. Pat. Nos. 4,298,685, 5,212,063, WO 92/21975 A, EP 1184 666 A2).

The result of a lateral flow assay is usually determined by a visual readout of the detectable signal. One or more detectable colored lines at the capture sites within the test zone indicate the presence of analyte in the sample, and the control line a successful chromato-graphic separation (cf. U.S. Pat. No. 5,229,073, DE 10 2008 028 908 B3). As mentioned, the captured label is proportional to the amount of analyte present in the probe and line intensities can be used to determine the absolute concentration of the analyte in the sampled probe. The intensity of the lines is, however, affected by the separation material, its porosity and thickness, the buffer and its pH, the age of the test, light conditions, eyesight, temperature and numerous other factors. Moreover, the human factor must be taken into account as there is an expectation of a certain result. This is a tremendous problem when the visual readout of a bedside flowthrough assay shall answer a life-critical question such as whether a newly born or preterm infant is suffering from a bacterial infection.

JP 5-5743 (Wakunga Pharmaceutical Co. Ltd) and WO 2013/122121 A1 (Sharp K K) describes a lateral-flow assay comprising a referential zone with a first immobilised capture antibody, a test zone with an immobilized capture and a third zone with another immobilised capture substance. The third zone serves as a positive control whether or not the test has been performed correctly. WO 2003/058242 A2 (Kimberly-Clark WW Inc.) discloses a lateral flow test wherein the referential or calibration zone defines one or more regions (e.g. dots, lines, etc.) containing differing amounts of capture antibodies configured to bind labeled conjugates. As a result, calibration signals are generated that can be compared visually to a test signal to determine the presence or quantity of an analyte in a test sample. The current lateral flow assays, however, allow no point-of-care diagnostics even when a scanner is used for an evaluation of the intensities of the labeled lines (cf. CN1455242A, WO2005/066624A1, EP 2 927 688 A1, EP 2 835 643 A1, EP 1 605 249 B1, US20090211345). Most importantly, there are no biomarkers which allow a conclusive and clear answer whether a neonate is suffering from a bacterial infection. The detection of bacterial infections in neonates is currently done, if at all, by culturing which takes long and is time-consuming. The numerous PCR methods produce pathogen-specific results but tend to produce false positive results and inconclusive answers. Thus, there are no rapid tests available for detection and bedside stratification of a bacterial infection in neonates with unspecific or unclear symptoms. The state of the art, therefore, represents a problem.

SUMMARY OF THE INVENTION

Disclosed herein is a point-of-care test device for detection and diagnosis of bacterial infections and septic processes in a sample of bodily fluid of a neonate, in particular of a preterm infant and newly born infant, comprising at least two quantitative flowthrough test units adapted for parallel detection and measurement of two different proteins of the S100 family of calcium-binding proteins, and in particular for several detection and measurement of an increased concentration of S100A12 and an increased concentration of calprotectin (calgranulin, S100A8/S00A9 complex) in a sample of bodily fluid, notably blood, serum, plasma, saliva. S100A12 and calprotectin are proteins released by cells of the congenital innate immune system and indicate different modes or stages of activation. The presence of S100A12 in the circulation (blood, serum or plasma) indicates an early activation of neutrophil granulocytes in response to a bacterial invasion whereas calprotectin is a contained in the basophilic granules of mast cells, monocytes and macrophages and primarily released in the course of a subsequent inflammation reaction. Both biomarkers are needed for bedside stratification of a bacterial infection in neonates with unclear symptoms as the unclear symptoms require clarification and explanation. More precisely, if a preterm or newly born infant shows symptoms of fever a bedside test giving a positive diagnostic result is needed. An excluding diagnostic result—no bacterial infection detectable—would not be considered trustworthy regardless whether it is based on a biomarker or a PCR method or even more sophisticated methods. The holistic answer to the unclear symptoms on basis of complementary biomarkers of the congenital innate immune system therefore provides a solution to the stated problems.

The present disclosure therefore provides a point-of-care test kit for bedside stratification of bacterial infections and septic processes in a bodily sample of a neonate, in particular of a preterm and/or newly born infant, comprising one or more flowthrough immunobinding assays for quantitative or semi-quantitative detection and measurement of at least two proteins of the S100 family of calcium-binding proteins, including at least a separate and several determination of S100A12 and calprotectin (S100A8/A9); and a blood sampling system for diluting a defined amount of blood sample in a defined amount of buffer which buffer does not induce an uncontrolled release of proteins from blood cells, granulocytes, monocytes, mast cells or leukocytes and allows for a quantitative flow-through immunobinding assay of the S100 protein analytes.

In some embodiments, the point-of-care test kit may comprise two separate flowthrough immunobinding assays in one housing adapted to produce visual zones indicating the presence and content of the analytes (T) in the sample and respective control zones (C). The point-of-care test kit is preferably adapted to co-operate with a portable processor device comprising a digital camera, a source of light and a processor configured to process digital images captured by said camera and to represent a diagnostic result.

In some other embodiments, the point-of-care test kit comprises a blood sampling system with an acidified buffer of a pH between 5.0 and 5.7 for the preservation of blood cells, containing citric acid, sodium citrate, monobasic sodium phosphate, dextrose and adenine. The acidified preservative buffer may comprise per litre 20-30 g trisodium citrate, 2.0-5.0 g citric acid, 2.0-5.0 g monobasic sodium phosphate (NaH$_2$PO$_4$), 0.1-0.5 g adenine, and may be mixed with blood in a ratio of about 1:5 to 1:10.

In some embodiments the point-of-care test kit may have one or more lateral flow test strips which comprise a size-exclusion technique, comb, mesh, weir-type filter structure, microporous fleece or fabricated porous filter membrane for retention of particulate blood components and blood cells from the liquid portion (serum, plasma).

An aspect of the disclosure pertains to a method of in vitro diagnosis and detection of bacterial infections and hidden septic processes in capillary blood or whole blood of a patient, notably premature and newborn babies, comprising mixing a predefined amount of bodily fluid, capillary blood or whole blood with a predefined amount of acidified buffer having a pH in the range from 5.0 to 5.7 and a functional amount of preservative; applying predefined amounts of the acidified mixture onto the application zones of one or more lateral flow immunoassays and performing a lateral flow immunochromatography for determination of both S100A12 and calprotectin, and comparing the amounts of both S100A12 and calprotectin in the visual zones with samples from healthy subjects. Increased amounts of S100A12 and calprotectin indicate a bacterial infection, a septic process or an inflammation in the patient.

In some preferred embodiments, a photographic image of the lateral flow immunoassay is taken, and the diagnostic result determined on basis of a digital photographic image using data of the visible zones and calibration data provided by the manufacturer. The method represents a quantitative or semi-quantitative determination of activation markers of the innate immune system. In a preferred embodiment, the method may comprise: (a) taking a digital image of the lateral flow immunoassay using a portable processor device, wherein said processor is configured to process digital images captured by said camera and to represent an analytical result; (b) analyzing the digital image for the location of the region of interest of said one or more lateral flow tests and for the amounts of signal.

In some preferred embodiments, the method is for simultaneous detection of S100A12 and calprotectin, comprising two lateral flow immunoassays having in fluid communication:—(i) a sample pad at the proximal end for receiving the sample, followed by (ii) a size-exclusion technique, comb, mesh, weir-type filter structure, microporous fleece or fabricated porous filter membrane for retention of particulate blood components and blood cells from the plasma portion; (iii) a conjugate pad containing mobile labeled immunoreactants which bind to the analyte, (iv) a membrane with porous separation material thereon, and (v) a water-adsorptive wicking pad at the distal end, wherein the separation membrane defines a proximal test zone containing immobilized capture molecules which bind to either analyte and a distal control zone for receiving mobile labeled immunoreactants.

Another aspect of the disclosure is a packaged kit for detection of bacterial infections and hidden septic processes in samples of bodily fluids of premature and newborns, characterized by a lateral flow immunoassay with a housing wherein are arranged in parallel two lateral flow immunochromatography test strips for simultaneous determination of calprotectin and S100A12 in capillary blood or whole blood; a blood sampling device for taking a defined amount of blood sample of 1 to 50 microliters; and a vessel containing a predefined amount of dilution and running buffer of a pH of 5.0 to 5.7 comprising a functional amount of blood preservative and anticoagulant, which vessel is suitable for separation of the particulate blood components from the plasma portion. The kit may further comprise a size-exclusion technique, comb, mesh, weir-type filter structure, microporous fleece or fabricated porous filter membrane for retention of particulate blood components and blood cells from the plasma portion.

The crux of the disclosed invention is a method for simultaneous detection of S100A12 and calprotectin (S100A8/A9 complex) in a sample of blood, plasma or serum or saliva using a separate lateral flow immunoassay. Each immunoassay may comprise in fluid communication (i) a sample pad at the proximal end for receiving the sample, followed by (ii) a filter pad, (iii) a conjugate pad containing mobile labeled immunoreactants which bind to the analyte, (iv) a membrane with porous separation material thereon, and (v) a water-adsorptive wicking pad at the distal end. The separation membrane may define a proximal test zone containing immobilized capture molecules which bind to either analyte and a distal control zone for receiving mobile labeled immunoreactants.

In some embodiments, the point-of-care test device for simultaneous detection of S100A12 and calprotectin may comprise a quantitative flowthrough unit, wherein the separation membrane defines a proximal test zone containing immobilized capture molecules which bind to either analyte and a distal test zone containing other immobilized capture molecules binding immunoreactant molecules. The unit may comprise a conjugate pad containing at least two types of mobile immunoreactants conjugated to the same type of label, which immunoreactants have differing binding properties. A first type of immunoreactant may bind to the analyte to form a labeled complex, and a second type of immunoreactant cannot not bind the analyte in the test sample. The mobile immunoreactant which does not bind to the analyte in the test sample may be contained in the conjugate pad in a set predetermined amount, while the mobile immunoreactant which binds to the analyte may be present in excess in the conjugate pad. A separation membrane may define at the distal end a second test zone with immobilized capture molecules that specifically bind the immunoreactant which does not form a complex with the analyte. A set of label may be obtained in the second test zone which is not influenced by the binding of the other mobile immunoreactant to the analyte and a capture of the labeled complex in the first test zone. Analysis of a digital photographic image of the second test zone may therefore serve as a pre-set color reference and control for a quantitative analysis and independent determination of the label in the analysis of a digital photographic image of the first test zone. The amount or concentration of analyte in the test sample may be determined on the basis of a digital photographic image of the entire lateral flow test device.

In another embodiment, the lateral flow assays may be incorporated in a cassette or envelope with defined openings for an application of a test sample on the sample pad and for a photographic imaging of the test zones.

In a further embodiment, the cassette may have printed markers which indicate the one or more positions of the first test zone and optionally a marker which indicates the spatial arrangement of the second test zone comprising the color reference for the photographic image. Optionally an individual test code in the form of a barcode or a two-dimensional quick reading code (QR) may be provided which allows making use of an external calibration curve (standard curve) when determining the intensity of the coloring within the first test zone.

An aspect of the disclosure relates to an in vitro diagnosis of bacterial infections and hidden septic processes in prematures and newborns comprising a parallel determination of both S100A12 and calprotectin using lateral flow immunoassays and by taking a photographic image of the lateral flow immunoassay using a smart phone and a smart phone application (APP). The diagnostic result may be determined thereby using a smartphone on basis of the digital photographic image and calibration data provided by the manufacturer via the internet.

In some embodiments, the method of the disclosure may comprise a quantitative or semi-quantitative determination of two separate markers of the innate immune activation in samples of bodily fluids of premature and newborns. The method may comprise the steps of (a) taking a color digital image of the lateral flow immunoassay using a camera; (b) analyzing the color digital image for the location of the second test zone and for the actual amount of label found in the second test zone; (c) comparing the actual amount of label found in the second test zone with a set amount of label in the second test zone to determine the offset of the digital image of the second test zone within one or more color channels from a set digital image of the second test zone; (e) correcting the actual digital image on basis of the set amount of label in the second test zone while also performing a white balance to adjust for the color temperature of the ambient light and/or supportive flashlight and, optionally, for the optical properties of the camera used for the taken color digital image; (f) analyzing the corrected color digital image for the location of the first test zone and for the amount of amount of label found in the first test zone; and (g) determining the amount of analyte contained in the test sample by comparison with the label values of a series of calibrated standards when determined by lateral flow immunoassays of the same lot of production.

An aspect of the invention is a kit for detection of hidden septic processes and bacterial infections in samples of bodily fluids of neonates by several detection of biomarkers released by cells of the congenital innate immune system, namely S100A8/A9 (calprotectin) and S100A12. The kit may comprise in duplicate or in triplicate or in a multitude as needed, sample pads for receiving the liquid sample, filter pads for filtering the test sample and homogenization of the flow-through in wicking direction, conjugate pads comprising mobile immunoreactants conjugated to a label, a membrane with porous separation material thereon, and a water-adsorptive wicking pad, wherein the separation membrane defines at least one first test zone comprising immobilized capture molecules for the analyte and one control zone for receiving labeled immunoreactants. Said kit is characterized in that calprotectin and S100A12 are analytes determined in parallel.

In some embodiments, said kit may comprise a conjugate pad comprising at least two types of labeled, but immunogenically and functionally distinct mobile immunoreactants. One mobile immunoreactant may bind to the analyte to form a labeled complex and the other may be inactive with respect to the formation of a complex with the analyte. The label reaction in the second test zone may be fully independent from the reaction of the other labeled immunoreactant with the analyte and the capture of the labeled complex in the first test zone. The inactive labeled immunoreactant may be provided in the conjugate pad in a predetermined amount so as to provide a color reference when a photographic image of the lateral flow test device is taken.

It is in particular an object of the invention to provide a point of care test which is sufficiently fast and reliable for detection of bacterial infections and hidden septic processes in samples of bodily fluids of premature and newborns. Calprotectin and S100A12 belong to the S100 family of proteins, which have a plethora of still to be defined functions in the host defense and immuno-regulation. It has been found that they are both sensitive markers of the innate congenital immune activation and that they can therefore be used to detect septic processes even in premature and newborn babies who not yet have a fully developed immune system. The presence of plasma or serum S100A12 is indicative for bacterial infections in prematures and newborns which are otherwise hard to distinguish from inflammatory processes.

The present disclosure contemplates immediate quantitation using a smartphone and suitable software for diagnosis of bacterial infections and sepsis in prematures and newborns. This provides an easy-to-cost-effective POCT (point-of-care test) which allows, quickly and easily, positive exclusion of bacterial infections in premature and newborns with unspecific symptoms. This can only be achieved by a determination of the serum or plasma levels of calprotectin and S100A12 as positive biomarkers of the innate congential immune system. This is because S100A12 is released by neutrophil granulocytes upon contact with bacteria in the blood stream. The neutrophil granulocytes belong to congenital immune system neutrophils represent about 70% of the granulocytes in blood. They are the first defense barrier to a bacterial invasion. The neutrophils require no further related signal or impetus to react on upon bacteria. The S100A12 protein further has antibacterial activity by competing about the essential calcium ions. A determination of the amount of S100A12 in a sample of bodily fluid therefore provides reliable information in case of unspecific symptoms. An increased calprotectin level in serum on the other hand indicates the onset of an inflammatory response on basis of cells of the innate immunity which may also give rise to unspecific symptoms. When both S100A12 and calprotectin are increased in serum, then the symptoms are due to a bacterial invasion which may have already given rise to an inflammation. When the S100A12 level only is increased in serum then neutrophil granulocytes had contact with bacteria in the blood stream which is also a indication for a treatment with antibiotics and further diagnosis. When calprotectin only is increased in serum—with no signs of an increased serum S100A12 level—then the unclear symptoms relate to an inflammation. With such a fast and reliable test there is no longer a need for a prophylactic antibiotic therapy upon appearance of unspecific symptoms or fever in neonates.

An increased S100A12 level in serum or blood is an innate biomarker for a bacterial invasion. An increased calprotectin level in serum or blood is an innate biomarker for an inflammatory response. If both S100A12 and S100A8/A9 are increased, the bacterial invasion has likely given rise to an inflammatory response. If the serum calprotectin (S100A8/A9) level is increased and serum S100A12 level below threshold, this is a useful surrogate for differentiating a bacterial infection from an inflammation. If both calprotectin and S100A12 levels are below thresholds, the innate immune system has not become activated. It seems therefore appropriate that the dual lateral flow test is adapted to become quantitatively evaluated using a smartphone camera in order to record the visual tests.

The principles of the disclosed invention will now be further described by reference to its advantages, drawings, embodiments and representative examples which shall not limit the gist of the invention that can be derived from the disclosure contained in the claims.

DETAILED DESCRIPTION OF THE INVENTION

Figure 1:
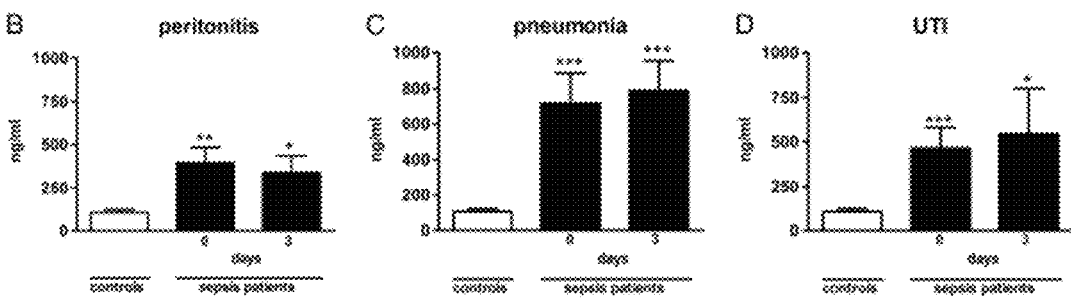
FIG. 1 shows a plot wherein the abszissa values represent the S100A12 concentration in serum sample of sepsis patients suffering from various types of bacterial infections.

Sepsis can be described as whole body inflammation in response to microbial infection which may lead to organ dysfunction and death. Among the about 760.000 births in Germany in 2018, about 10% are premature. Prematures are generally transferred to a neonatal intensive care unit where almost all of them received a prophylactic antibiotic therapy since preterm infants and newborns are particularly vulnerable to life-threatening bacterial infections. Despite advances in neonatal intensive care, bacterial infections still are a main cause of morbidity and mortality in neonates. The mechanisms underlying this heightened susceptibility of preterm infants and newborns to sepsis and bacterial infections are not fully understood. Emerging data suggest that the immune responses are still deficient in preterm and newly born infants and that the congenital innate immune system is key for a protection against infections early in life. Early and differential detection of a bacterial invasion is critical but not available for newborns and preterm infants so that they receive a prophylactic antibiotic therapy upon first appearance of unspecific symptoms or fever. On the other hand, in approximately 5% of the cases only a bacterial infection can be demonstated using culturing methods (Cailes B et al, *The current and future roles of neonatal infection surveillance programmes in combating antimicrobial resistance*, Early Hum Dev. 2015, 91(11):613-8).

The prophylactic antibiotic therapy causes problems. First, a continuous increase in the proportion of multi-resistant gram-negative pathogens (MRGN) in newborns. A study revealed that 85% of the *Escherichia coli* pathogens in newborn sepsis were resistant against ampicillin in 2002 (Stoll B J et al, *Changes in pathogens causing early-onset sepsis in very-low-birth-weight infants*, N Engl J Med. 2002, 347(4):240) and some pathogens were even multi-resistant against two antibiotic groups (*Epidemiologisches Bulletin, Robert Koch Institut,* 21 Okt. 2013/Nr. 42). Second, the colonization of the newborn with microorganisms begins immediately after birth which represents a transition from a 'sterile' intrauterine existence through the colonized birth canal into largely peaceful coexistence with a myriad of microorganisms. Those microorganisms can be commensals or potentially invasive pathogens. This holds two seemingly contradictory challenges for the newborn: (a) recognition and efficient elimination of potentially invasive pathogens and (b) controlled coexistence and tolerance of commensals on skin and mucosal surfaces. The microorganisms also contribute to the growth and development of the child, including the formation of the immune system as part of a healthy microbiota. An antibiotic therapy in prematures and newborns may therefore also have adversal effects on the composition of the microbiota and the child's early development. Reported side effects include an increased susceptibility to fungal infections as well as an increased risk of diseases such as asthma, overweight, etc. (Saari A et al, *Antibiotic exposure in infancy and risk of being overweight in the first 24 months of life*, J Pediatrics 2015, 135(4):617-26; Arboleya S et al, *Intestinal microbiota development in preterm neonates and effect of perinatal antibiotics*, J Pediatr. 2015, 166(3):538-44).

The risk of bacterial infection in neonates is largely dependent on gestational age and birth weight. While preterm infants constitute a small minority of all births, they contribute disproportionately to neonatal morbidity and mortality with sepsis and infection-related complications being the leading cause of adverse outcomes and death. The high risk of bacterial infection in preterm infants has a number of determinants: first, extremely preterm infants require prolonged intensive care, including mechanical ventilation, parenteral feeding, and intravenous access, which breach physical barriers against infection. Second, the increased susceptibility of the preterm infant can render innocuous microorganisms pathogenic. Third, the pathways of the acquired immune system function may not be functional. There is evidence that the infection-driven inflammation can also contribute to the adverse outcomes in the form of chronic lung disease and neurodevelopmental impairment.

Culturing of pertinent samples on selective agar media takes long time until results, sometimes up to one week, depending on the pathogen. Bacterial pathogens can also be identified by PCR methods but even the fastest PCR methods (e.g., the Roche LightCycler® SeptiFast Test) take hours. While PCR arrays can test for numerous microorganisms this technique has a record of producing too many false positives and clinically non-relevant results since it is not quantitative and cannot truly distinguish between innocuous, pathogenic and life-threatening microbes. When a newborn is observed having fever and the PCR method produces as a diagnostic result that no bacterial strain was detectable, it is therefore concluded that there must have been an error with the complex method or the sample. On the other hand, when the PCR test array always shows the presence of one or more microbial strains, this finding may not be clinically relevant and the result of a non-specific contamination. Doctors and nurses do not wish to rely on complex tests.

On the other hand, rapid tests for the detection of pathogenic bacteria or toxins test for the presence of one particular pathogen only at a time, e.g. for *Clostridium difficile*, which is responsible for diarrheal diseases. C-Reactive protein (CRP), white blood cell counts, tumour necrosis factor-α, interleukins (IL-6) are further used as clinical biomarkers for sepsis. The levels of CRP are increased in blood during bacterial infections but cannot be consistently detected over the course of an infection. CRP levels increase 24 to 48 hours after an infection and IL-6 is only present during the first hours of an infection. However, the relevant signal transduction pathways are sometime not established in prematures and newborns. These biomarkers cannot be relied on for diagnosing sepsis in preterm infants as they may also be elevated for other reasons.

Procalcitonin (PCT) is further a generally used biomarker for a diagnosis of sepsis. Procalcitonin however can only be used for monitoring a response to antimicrobial therapy, diagnosis of secondary inflammations, diagnosis of renal involvement in paediatric urinary tract infection, etc. While procalcitonin levels are increased in blood during inflammation and bacterial infections, they may also be increased in blood due to non-infectious causes such as injury, damage to internal organs, surgical procedures, etc. The procalcitonin levels are therefore no useful biomarker for preterm and newly born infants for a differentiation between bacterial infections and other causes of inflammation.

While all types of microorganisms (bacteria, virus, fungi and parasites) can cause sepsis, bacteria are the most common pathogens. The bacteria can invade into the blood stream and proliferate locally while releasing virulent factors. These factors stimulate the release of endogenous mediators and the release of bactericidal proteins from neutrophil granulocytes of the innate immune system. This sepsis-related inflammatory response is triggered when the body attempts to neutralize the pathogen which in turn leads to an activation of the immune system to secrete inflammatory proteins which can damage tissues and organs.

The term "S100 proteins" is used for a family of low-molecular-weight proteins found in vertebrates and characterized by two calcium-binding sites that have helix-loop-helix ("EF-hand type") conformation. The S100 proteins are part of the congenital innate immune system that blunts the response to an infection together with the complement system. The present disclosure therefore suggests a use of these S100 proteins as biomarkers of the congential innate immune system for a differential diagnosis of a bacterial invasion, sepsis and other inflammatory reactions. It has been found that the S100A12 proteins are primarily expressed in and released from neutrophils (neutrophil granulocytes) upon contact with bacteria in the circulation. S100A8/A9 or calprotectin (calgranulin) is expressed and released from macrophages, monocytes and mast cells in response to an inflammation or allergic reaction. There are at least 21 different S100 proteins (Marenholz I, Heizmann C W, Fritz G (October 2004). "*S100 proteins in mouse and man: from evolution to function and pathology (including an update of the nomenclature*" Biochem. Biophys. Res. Commun. 322 (4): 1111-22). The S100 gene family is clustered on chromosome 1q21 and includes at least 13 members named by a S100 prefix (e.g. S100A1, S100A2, S100A3). They are considered Damage-associated molecular pattern molecules (DAMPS) which activate pattern recognition receptors (e.g., Toll-like receptor 4, RAGE) which can mediate inflammation. The expressed S100 proteins are localized in the cytoplasmic granules of cells of the innate immune system, and they are released by these cells in the regulation of a number of physiological processes. The S100 proteins also include antimicrobial peptides with antibacterial activity. The the mode of action is likely by depleting essential metal ions that are required for the invading organism to grow and thrive. The S100 proteins have further likely a role in some calcium-dependent signal transduction pathways and regulatory effects on cytoskeletal components which can modulate various neutrophil activities. The S100A12 protein and the S100A8/A9 complex (calprotectin) have probably key roles in the innate immune response to pathogens and inflammatory reactions and as they are immediately released by their respective cells into the blood stream upon a bacterial invasion and in the course of an inflammation. They can therefore serve as biomarkers for a rapid stratification of a bacterial infection and inflammation in preterm infants and newborns.

The concentration of S100A12 and calprotectin in serum can be rapidly measured by a flowthrough binding assay within a few minutes if the innate immune system is not activated by the blood sampling and the quantitation be done promptly thereafter. The test kit therefore allows a stratification of bacterial infection as well as a continuous monitoring of the preterm and newly born infant. The disclosure herein further provides a point-of-care test device for detection and stratification of bacterial infections and hidden septic processes in bodily fluids of premature and newborns comprising a quantitative or semi-quantitative lateral flow immunoassay unit adapted for several detection of an increased plasma or serum concentration of S100A12 and an increased plasma concentration of calprotectin.

The protein S100A12 has many names, including CAAF1; calcium-binding protein in amniotic fluid-1, calgranulin C, calgranulin-related protein (CGRP), cornea-associated antigen (CO—Ag), extracellular newly identified RAGE-binding protein (EN-RAGE), protein of 6 kDa (P6); S100 calcium-binding protein A12. They all refer to a 10.4 kDa calcium-binding protein which is exclusively found in and released by activated granulocytes, more precisely neutrophilic monocytes and lymphocytes as well as some other types of lymphocytes. S100A12 is in humans encoded in the S100 gene cluster on chromosome 1 (Wicki R et al, "*Characterization of the human S100A12 (calgranulin C, p6, CAAF1, CGRP) gene, a new member of the S100 gene cluster on chromosome 1q21*" Cell Calcium 1997, 20 (6): 459-5 64. doi:10.1016/S0143-4160(96)90087-1). These granulocytes (70% of the total monocytes) form an essential component of the unspecific innate immune response and their primary role is to recognize and bind pathogens directly after their invasion into the organism.

Figure 2:
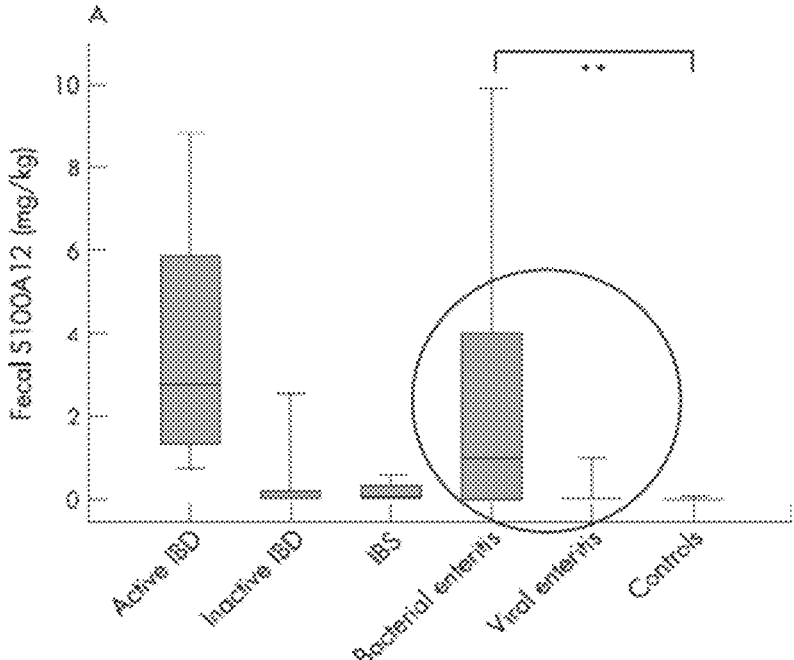
FIG. 2 shows a plot wherein the abszissa values represent the S100A12 concentration in serum samples of patients with inflammatory bowel disease (IBD) and infectious enteritis.

S100A12 is significantly increased in case of a bacterial invasion in prematures and newborns. The concentration of S100A12 in the serum of sepsis patients with different origins of infection (B) abdominal cavity, (C) lung, (D) urinary tract, at the beginning of the infection (day 0) and after 3 days versus healthy controls is shown in FIG. 1 ($*p<0.05$, $p<0.005$, $*p<0.0005$); see Achouiti et al, S100A12 and soluble receptor for advanced glycation end products levels during human severe sepsis Shock 2013, 40(3):188-94). The functions of S100A12 comprise a removal of the zinc and calcium in the signal pathways; being a chemotactic cytokine for monocytes and mast cells; in having antimicrobial activity and inhibiting matrixmetallproteinases; inducing toll-like receptor 4(TLR4)-activation, for activating the receptor for advance glycation action (RAGE). S100A12 is generally a biomarker of the inflammation response and further pro-inflammatory reactions in cells such as endothel cells, phagocytes, and lymphocytes. As S100A12 is secreted not via the Golgi apparatus but through an alternative pathway, its secretion cannot be inhibited or blocked. The present application discloses to use S100A12 as a biomarker in plasma or serum for distinguishing bacterial and viral infections not only in adults but in particualr in prematures and newborns. As shown in FIG. 2, S100A12 is significantly increased compared to healthy controls ($**p<0.01$) in case of an activation of the innate immune system, e.g. upon viral Infection (Kaiser T et al, "Faecal S100A12 as a non-invasive marker distinguishing inflammatory bowel disease from irritable bowel syndrome" Gut. 2007 December; 56(12):1706-13. Epub 2007 Aug. 3). Thus, the marker would allow distinction between active and inactive chronic inflammatory disease (IBD) but this indication occurs very rarely during the first 12 months of life.

S100A12 can therefore be detectable in babies as part of the congenital immune system. This system needs not to be acquired, in contrast to the adaptive, specific immune response. Non-specific symptoms and fever in premature and newborn babies are often induced by a non-dangerous virus infection, which does not require therapy. In these children, a prophylactic antibiotic treatment is an over-therapy with considerable side effects for their early development and it also contributes to resistance formation. The S100A12 can be tested in samples such as blood, urine, stool, respiratory tract fluids, saliva, etc. A comprehensive testing system for premature and neonates in blood is provided by the present invention. However, the presence of elevated concentrations of S100A12 alone in the samples from premature and newborns does not provide the desired certainty that an infection is of bacterial origin.

Calprotectin is the heterodimer of S100A8 and S100A9. Other names of S100A8 are 60B8AG; CAGA; calgranulin A; calprotectin L1L subunit; CFAG; CGLA; CP-10; cystic fibrosis antigen; L1Ag; leukocyte L1 complex light chain;

MA387; MIF; migration inhibitory factor-related protein 8; MRP-8; NIF; P8; p8; Protein S100-A8; S100 calcium binding protein A8; urinary stone protein band A. S100A9 is also known as 60B8AG; CAGB; calgranulin B; calprotectin L1H subunit; CFAG; CGLB; L1AG; leukocyte L1 complex heavy chain; LIAG; MAC387; MIF; migration inhibitory factor-related protein 14; MRP-14; MRP14; NIF; P14; protein S100-A9.

The term "calprotectin" stands fora complex of the mammalian proteins S100A8 and S100A9 (Lehmann, F. S.; Burn, E.; Beglinger, C. (13 Oct. 2014). "*The role and utility of faecal markers in inflammatory bowel disease*" Therapeutic Advances in Gastroenterology 8 (1): 23-36.; Trebichaysky, I (2004). "*Calprotectin—a pleiotropic molecule in acute and chronic inflammation*" Physiological research/Academia Scientiarum Bohemoslovaca 53 (3): 245-53). The complex has several synonyms, including MRP8-MRP14, calgranulin A and B, cystic fibrosis antigen, 60BB antigen, and 27E10 antigen. In the presence of calcium, calprotectin is capable of sequestering the essential nutrients manganese and zinc. This metal sequestration affords complex antimicrobial properties. Calprotectin comprises as much as 60% of the soluble protein content of neutrophil cytosol, and is secreted likewise not by the Golgi apparatus but by a so far unknown alternative mechanism. Faecal calprotectin is being widely used to detect intestinal inflammation, and serves as a marker for inflammatory bowel diseases.

The human homologue of calprotectin is a 24 kDa dimer and is formed by the protein monomers S100A8 (10,835 Da) and S100A9 (13,242 Da) (cf. UniProt "P05109-S10A8_HUMAN"; UniProt "P06702-S10A9_HUMAN" http://www.uniprot.org). The primary structure of calprotectin varies between species. For instance, the mouse homologue of S100A8 is 10,295 Da (UniProt "P27005-S10A8_MOUSE") while the S100A9 homologue is 13,049 Da (UniProt. "P31725-S10A9_MOUSE" http://www.uniprot.org). Early size exclusion chromatography experiments incorrectly indicated that calprotectin had a molecular mass of 36.5 kDa; occasionally this value is used in contemporary literature. Calprotectin S100A8-S100A9 dimers can non-covalently pair with one another to form 48 kDa tetramers.

According to the present disclosure, the simultaneous or parallel determination of S100A12 and calprotectin can provide the valuable clinical information whether an antibiotic therapy is required. The detection of elevated amounts of both S100A12 and calprotectin, at set predetermined levels, gives an unambiguous indication of an occuring bacterial infection even in premature and newborns because both proteins belong to the innate immune system. The combined simultaneous assessment of the levels of both S100A12 and calprotectin gives a meaningful diagnosis and allows to avoid unnecessary prophylactic antibiotic treatments.

In lateral flow immunchromatography, a fluid sample is drawn towards a zone where specific immobilized reagents—antibodies—reside. If the target molecule is present in the sample, the target binds to the immobilized antibody and can be visualized when coupled to a detectable marker, e.g. another antibody bearing a detectable marker such a gold nanoparticles. The term "antibody" as used herein contemplates a polypeptide or a protein complex that specifically binds an epitope of an antigen. An antibody includes an intact antibody, or a binding fragment thereof that competes with the intact antibody for specific binding and includes chimeric, humanized, fully human, and bispecific antibodies. Binding fragments include, but are not limited to, Fab, Fab', F(ab')2, Fv, and single-chain antibodies. In some embodiments, an antibody is referred to as an immunoglobulin and include the various classes and iso-types, such as IgA (IgAI and IgA2), IgD, IgE, IgM, and IgG (IgGI, IgG3 and IgG4) etc. In some embodiments, the antibody is polyclonal or monoclonal. In some embodi-ments, the antibody is from any origin, such as mouse or human, including a chimeric antibody thereof. In some embodiments, the antibody is humanized. The term "anti-body" as used herein also contemplates the biosimilar or second generation version of the monoclonal antibodies described herein.

The term "sample pad" as used herein generally refers to a hydrophilic element, such as a membrane that receives the antibody. In some embodiments, the sample pad is part of the conjugate pad, or a discrete pad positioned downstream of and in fluid communication with the conjugate pad. In some embodiments, the sample pad is useful for promoting the even and controlled distribution of the antibody onto the conjugate pad, controlling the rate at which the antibody enters the conjugate pad, or preventing flooding of the test device. In some embodiments, the sample pad material comprise of, but not limited to, for example, woven mesh or cellulose filters, glass fiber, mixed glass fiber and cellulose, man-made fiber, mixed fiber, surface modified plastic (poly-ester, polypropylene, or polyethylene), nitrocellulose, or graded density polyethersulfone (PES). In some embodi-ments, the sample pad is of the same or different material as the conjugate pad. In some embodiments, the sample pad is impregnated with agents to influence the flow rate of the sample, including, for example, protein detergents or sur-factants, viscosity enhancers, signal enhancers, or buffer salts. In some embodiments, agents are added to the sample pad to prevent the detectable marker and antibody from binding nonspecifically to any downstream materials or to modify the chemical nature of the antibody so that it is compatible to complex at the test line. In some embodi-ments, the sample pad further comprises a buffer, pH cali-brator, peptide, or antibody.

The term "conjugate pad" as contemplated herein, gen-erally refers to a hydrophilic element, such as a membrane, containing a conjugate reagent such as colloidal gold, latex particles, enzymes, colored dyes, or paramagnetic or fluo-rescent particles. In some embodiments, the conjugate pad acts to ensure uniform transfer of the detectable marker and the antibody onto the test membrane. In some embodiments, the conjugate pad comprises, but not limited to, woven mesh or cellulose filters, glass fiber, mixed glass fiber and cellu-lose, man-made fiber, mixed fiber, surface modified plastic (polyester, polypropylene, or polyethylene), nitrocellulose, or graded density PES. In some embodiments, the conjugate pad is part of the sample pad, or a discrete pad positioned upstream of, and in fluid communication with the sample pad. In some embodiments, the conjugate pad is of the same or different material as the sample pad. In some embodi-ments, the conjugate pad further comprises an antibody. In one of these embodiments, the antibody is an immunoglobu-lin antibody.

The term "test line" as contemplated herein, refers to a band or zone on the test membrane. In some embodiments, more than one test line is applied for multi analyte testing or for semi-quantitative evaluation. In some embodiments, the peptides in the test lines are conjugated to a protein.

The term "wicking pad" as used herein contemplates an absorbent pad attached at the distal side of the test device. The wicking pad aids to maintain the flow of liquid to the end of the strip. In some embodiments, the wicking pad comprises, but not limited to, an absorbent material, cellulose filter, or any other material which acts to maintain the flow of liquid to the end of the strip.

The term "plasma separation" comprises the removal of blood cells from plasma for downstream analysis and diag-nosis. Traditionally, plasma is extracted from blood in laboratories and clinics by centrifugation with conventional bench-top centrifuges which are known to be time consum-ing and labor intensive. However, during centrifugation the sedimented blood cells can easily lyse (RBCs hemolysis), thereby releasing intracellular components which contami-nate the plasma sample. To overcome this limitation, several microfluidic techniques for plasma isolation from blood have been developed. Perhaps the most common way of separating plasma from blood cells using microfluidic devices is based on the principle of particle retention. These devices involve the use of filters or meshes to retard or block blood cell movement, thereby allowing the collection of the plasma portion of blood. In particular, comb and weir-type filter structures with 0.5 µm gaps permits the passage of plasma while retaining gently the RBCs, leukocytes, granu-locytes, monocytes and other platelets. Size-exclusion based techniques relying on integrated microporous fleece or membranes have also been developed.

It is a general object of the present disclosure to provide methods, devices and kits used to visually determine the presence or absence of a specific, biologic and/or to visually quantify or semi-quantify an amount of a specific, biologic such as calprotectin and/or S100A12. It is also a general object of the present disclosure to provide methods, devices and kits which is used to visually determine the presence or absence of a specific biologic and/or to visually quantify or semi-quantify an amount of a specific biologic. In preferred embodiments, it will be readily appreciated that other detec-tion systems, optical or otherwise, is used in such tests. A most preferred detection is a system using the CCD camera of a smart phone or similar device together with software for telemedicine and calibration of the readings.

In one embodiment of the present disclosure, the test device includes qualitative readout (e.g., presence/absence of a specific protein). Semi-quantitative or quantitative results are also contemplated. In some embodiments, semi-quantitative or quantitative results is achieved by including a series of test lines of increasing concentration. In some embodiments, the test device of the present disclosure detects active protein at least about 30, 40, 50, 60, 70, 80, 90, or 95% activity. In certain embodiments, evaluation of the signal intensity is also performed. In some embodiments, the signal is digitized and evaluated using a flatbed scanner or a CCD camera (e.g. the camera of a so-called smart phone and appropriate software. In some embodiments, sensitivity is increased by use of enhancement agents such as, for example, a silver enhancer. More sensitive chemilumines-cent or fluorescent labels are optionally used to increase the sensitivity as well. Free peptide, to compete for binding with the protein, is optionally included in the conjugate pad to threshold the assay, when decreased sensitivity is desired. In some embodiments, sensitivity is also controlled by adjust-ing, for example, the bed volume of the membrane, dimen-sions of the test membrane, porosity of the test membrane, position and width of the test line and control line.

In one embodiment, the test device is a lateral flow immunoassay. In one embodiment, the lateral flow immu-noassay format is chosen from antigen sandwich assay, antibody assay, or competitive hapten assay.

In one embodiment, the sample pad of the test device further comprises a buffer for pH stabilization, a pH calibrator, a surfactant to guarantee a uniform wetting, a stabilizing polymer, and a blocker. The position of the sample pad often varies.

In one embodiment, the protein is introduced to the sample pad using a dipstick format and contacting one end of the test device with the protein. In another embodiment, the protein is introduced onto the sample pad using an applicator such as, for example, a pipette, a syringe, a dropper, a spray, and others known in the art. The protein amount is received on the sample pad in a volume preferably between about 1 and 400 μl, more preferably between about 3 and 200 μl, and most preferably between about 5 and 100 μL.

In one embodiment, the sample pad of the test device receives a protein in a fluid selected from the group consisting of buffer, saline solution, and biological fluid. In another embodiment, the biological fluid received by the sample pad is selected from a group consisting of body fluids or extracts of blood, serum, urine, faeces, saliva, respiratory tract fluids.

In one embodiment, the conjugate pad of the test device comprises a detectable marker. In another embodiment, the detectable marker in the conjugate pad is capable of binding the protein that the sample pad receives. In one embodiment, the conjugate pad acts to ensure uniform transfer of the detectable marker and the protein onto the test membrane. In one embodiment, the detectable marker comprises, but not limited to, particles, luminescent labels, calorimetric labels, fluorescent labels, chemical labels, enzymes, radioactive labels, metal colloids, and chemiluminescent labels. In one embodiment, gold colloidal spheres are used. In another embodiment, other metal sols and latex microparticles are used as well. In other embodiments, photostable, color tunable nanoparticles such as carbon, selenium, or quantum dots are used as detectable markers. These detectable markers provide colorimetric indicators for reporting whether the target molecule is present. The size of the detectable markers are related to the porosity of the membrane. The markers are preferably sufficiently small to be transported along the membrane by the capillary action of the fluid. In one embodiment, the amount of detectable marker present varies depending on the size and composition of the detectable marker, the composition of the membrane, and the level of sensitivity of the assay. The detectable marker will bind to the protein to form a protein-detectable marker complex. In one embodiment, the detectable marker comprises gold colloidal spheres. In another embodiment, the detectable marker comprises a secondary protein. In some embodiments, the secondary protein is an antibody. In some embodiments, the secondary protein is conjugated to gold.

In one embodiment, the method of determining the presence or integrity of a protein comprises a test device wherein the test device is a lateral flow assay. In another embodiment the sample pad in the method further comprises a buffer, pH calibrator, peptide, or antibody.

In one embodiment of the method disclosed herein, the conjugate pad comprises a detectable marker. In another embodiment of the method disclosed herein, the detectable marker is selected from a group consisting of: particles, luminescent labels, calorimetric labels, fluorescent labels, chemical labels, enzymes, radioactive labels, metal colloids, and chemiluminescent labels. In another embodiment of the method disclosed herein, the detectable marker comprises gold colloidal spheres.

In one embodiment of the method disclosed herein, the detectable marker comprises a secondary protein. In one embodiment, the secondary protein is an antibody. In another embodiment of the method disclosed herein, the secondary protein is conjugated to gold.

In one embodiment of the method disclosed herein, the test membrane comprises at least one test line and at least one control line. In another embodiment of the method disclosed herein, the test membrane comprises two or more test lines.

One embodiment of the present disclosure comprises a kit comprising (a) a test device for determining quantitatively or semi-quantitatively the presence of proteins of the S100 family, as described above, and (b) instructions for use thereof. In another embodiment, the kit may further comprise a protein sample. In another embodiment, the kit further comprises a protein applicator. In another embodiment, the protein applicator is, for example, a pipette, a syringe, a dropper, or others known in the art.

In one embodiment, if trace amounts of the S100 proteins give a positive result, free S100 peptides are added to the conjugate pad. Those free peptides compete for the protein in the sample and its concentration will determine the threshold amount required for detection. The precise threshold will ultimately depend on the point of use, in particular whether the test is to be performed on the antibody as packaged in the shipping vials or after mixing for infusion.

In another embodiment, the detectable marker in the conjugate pad is capable of binding the antibody that the sample pad receives. In one embodiment, the conjugate pad acts to ensure uniform transfer of the detectable marker and the antibody onto the test membrane. In one embodiment, the detectable marker comprises, but not limited to, particles, luminescent labels, calorimetric labels, fluorescent labels, chemical labels, enzymes, radioactive labels, metal colloids, and chemiluminescent labels. In one embodiment, gold colloidal spheres are used. In another embodiment, other metal sols and latex microparticles are used as well. In other embodiments, photostable, color tunable nanoparticles such as carbon, selenium, or quantum dots are used as detectable markers. These detectable markers provide colorimetric indicators for reporting whether the target molecule is present. The size of the detectable markers are related to the porosity of the membrane. The markers are preferably sufficiently small to be transported along the membrane by the capillary action of the fluid. In one embodiment, the amount of detectable marker present varies depending on the size and composition of the detectable marker, the composition of the membrane, and the level of sensitivity of the assay. The detectable marker will bind to the antibody to form an antibody-detectable marker complex. In one embodiment, the detectable marker comprises gold colloidal spheres. In another embodiment, the detectable marker comprises a secondary antibody. In some embodiments, the secondary antibody is conjugated to gold. In some embodiments, the test device further comprises a wicking pad.

In one embodiment, the method of determining the presence and amount of S100 proteins in a sample comprises a test device wherein the test device is a lateral flow immunoassay. In another embodiment the sample pad in the method further comprises a buffer, pH calibrator, peptide, or antibody. In one embodiment of the method disclosed herein, the conjugate pad comprises a detectable marker. In another embodiment of the method disclosed herein, the detectable marker is selected from a group consisting of: particles, luminescent labels, calorimetric labels, fluorescent labels, chemical labels, enzymes, radioactive labels, metal colloids, and chemiluminescent labels. In another embodiment of the method disclosed herein, the detectable marker comprises gold colloidal spheres. In some embodiments, the test device of the present disclosure has a protective cover. In some embodiments, the protective cover is formed of any material which is impervious to water, and is preferably translucent or transparent. In certain embodiments, the protective covering or cassette comprises a single or multiple layers. Preferable materials for use in the protective cassette include materials such as polyamide, polyester, polyethelene, acrylic, glass, or similar materials. The protective covering is optionally clear (i.e., see-through) or not clear (i.e., opaque) depending on the method of detection used. In a preferable embodiment, a protective covering is optically clear polyester.

The QuantOn technology has successfully been applied in the detection of calprotectin—S100A8/A9—(QuantOn-Cal®), allowing for fast, sensitive, and quantitative evaluation without laboratory equipment. The QuantOn technology can be easily applied to the measurement of S100A12. Patient data are directly available and digitalized, i.e. it can be easily documented and, for example, an increase in S100A12 concentration can be tracked over several days. With QuantOn® technology adapted to the parallel measurement of S100A12 and calprotectin, fast and sensitive quantitative analysis of samples can be performed directly on site without any laboratory equipment. The measured values are particularly meaningful because measurement is performed directly after sampling, so that the concentration of either biomarker in the sample is not altered by the otherwise usual pre-analytic events (transport, standing time, temperature changes etc.).

In summary, a lateral flow test for the simultaneous parallel detection of S100A12 and calprotectin in samples of premature and newborns is provided. For the implementation, the QuantOn® software is used for measuring data acquisition, interface to clinic system, data preparation and corresponding presentation. Clinical validation of the test procedure is, thus, provided. For test performance, a test unit is contacted with the sample of a premature or newborn, and evaluated with the smartphone application for diagnosis, so that easy integration into routine diagnostic procedures by clinical users is provided.

Therefore, there is currently no rapid test to exclude a bacterial infection in premature and newborn babies with comparable advantages. Since the significance of interleukin-6 in premature and newborn is low, the parallel simultaneous determination of both S100A12 and calprotectin offers superior clinical information.

The QuantOn® technology provides a quick test procedure with visual evaluation. By evaluating with the smartphone, a quantitative, digital measurement value is obtained, which is independent of the subjective assessment of the evaluating person. In addition, the error rate during test execution is minimized by the QuantOn® technology. The smartphone application guides the user safely through the test execution and controls the timing for preserving unadulterated readings (first, the incubation time of the lateral flow test; second, the time to evaluate the test result by the recording camera of the smartphone). The test requires 15 minutes, and can be then evaluated within 2 minutes with the smartphone application. With the existing diagnostic solutions, no rapid statement can be provided with regards to the presence of a bacterial infection in premature and newborns.

Currently, lack of sensitive, fast and cost-effective test methods together with high mortality and morbidity rates in sepsis, lead clinicians to apply prophylactic antibiotic therapy in premature and newborns having unspecific symptoms or fever. This approach contributes significantly to increase the occurrence of antibiotic resistance, which is particularly critical in this group of patients, and has a negative impact on early childhood development.

The present diagnostic procedure is cost-effective, easy to handle, user-friendly, specific and sensitive. The result is obtained within minutes after sampling. Following the present method, the prophylactic use of broad spectrum antibiotics may be omitted in cases where unspecific symptoms or fever are due to non-bacterial causes. Accordingly, the POCT of the disclosure is suitable for distinguishing bacterial from viral infections in premature and newborns and, thus, for deciding whether to use antibiotics for treatment. Avoidance of costly antibiotics, in particular broad spectrum antibiotics, for treatment of infections which are not caused by bacteria is provided by use of the disclosed POCT. Rapid diagnosis for the exclusion of bacterial pathogens from the diagnosis may be achieved.

The following examples are provided to further illustrate the embodiments of the present disclosure, but are not intended to limit the scope of the disclosure. While they are typical of those that might be used, other procedures, methodologies or techniques known to those skilled in the art may alternatively be used.

EXAMPLES

Example 1 Parallel Measurement of Human S100A12 and Calorotectin in Newborns The concentration of S100A12 and calprotectin were determined in saliva in a pilot study with 10 newborn subjects. S100A12 and calprotectin levels were determined by means of a semi-quantitative lateral flow immunoassay unit (Immundiagnostik AG) adapted for parallel detection. The unit comprised a cassette having two independent lateral flow immunoassay strips for determination of S100A12 and calprotectin, respectively. The cassette had proximally one opening to allow application of the sample on the proximal zone of the strip. 200 µL saliva from each newborn were mixed with 200 µL 1×PBS and applied into the proximal opening. The proximal zone comprised gold-labeled mouse monoclonal antibodies against either S100A12 or calprotectin, which antibodies can diffuse in direction to the distal end of the strip upon contact with an aqueous solution. One distal opening for visualization of the test and control zones is provided. The test zone also comprised antibodies against either S100A12 or calprotectin. The antibodies in the test zone were immobilized onto the strip so that they could not diffuse. The binding to the immobilized antibodies to either S100A12 or calprotectin, which previously bound to gold-labeled mouse monoclonal antibodies in the proximal zone, resulted in a colored band in the test zone. Gold-labeled mouse monoclonal antibodies which do not bind to S100A12 or calprotectin diffused into the most distal control zone. This control colored band indicates that the test is performed correctly. After 15 minutes, a smartphone with Immundiagnostik's proprietary QuantOn® software installed was used to obtain an image of the colored bands. A colored band of defined intensity in both test zones of the lateral flow immunoassay strips indictaed that the newborn was subject to a bacterial infection or an inflammation. The QuantOn® software allowed a non-visual discrimination of color intensity and, consequently, for the presence or absence of a bacterial infection.

Example 2 Clinical Feasibility Study

To demonstrate the clinical feasibility of this approach, calprotectin and S100A12 levels were compared with the results of microbiological cultures from saliva and with multiplex PCR covering germs most frequently encountered in bacterial infections in newborns. For categorization of results, different levels of calprotectin and S100A12 are classified as follows: low, moderately increased, and markedly increased. A microbiological culture is deemed "negative" if after the established incubation time for the different types of culture (aerobic, anaerobic) no organism is identified. The PCR results is deemed "positive" if the reading yielded at least grade 2 on a five-grade scale (0, negative; 1, very faintly positive; 2, faintly positive; 3, positive; 4, markedly positive).

In summary, the determination of calprotectin and S100A12 levels in saliva samples of newborns with the present POCT gave comparable information as microbiological diagnostics, however, in a much shorter period of time. It therefore seems appropriate to extend this technique to the analysis of blood of newborns to allow detection of a bacterial invasion into the bloodstream.

Example 3 Preservative Anti-Coagulant Running Buffers

Several running and dilution buffers were tested. A useful preservative anti-coagulant running buffer system for blood may contain acidified citrate dextrose (ACD) or citrate-phosphate-dextrose (CPD) which are used to maintain 2,3-diphosphoglycerate (2,3-DPG) levels in blood. Acidified citrate-phosphate-dextrose with adenine (CPDA-1) preservative which improves the synthesis of adenosine triphosphate (ATP) in the blood sample is preferred. Most preferred are acidified anti-coagulant running buffers which have been "energized" by the addition of ATP. A most preferred preservative/anti-coagulant running buffer may contain per liter 20.00 to 30.00 g trisodium citrate; 2.5 to 3.0 g citric acid, 20.0 to 40.0 g dextrose or mannitol, about 2.0 to 3.0 g monobasic sodium phosphate, and 0.2 to 0.4, as well as distilled water. The pH of the running buffer may be between a pH of 5.0 and 5.70 so that calprotectin (S100A8/A9) and S100A12 which have isoelectric points in the range between 5.7 and 6.6 do not precipitate on the separation membrane. The reported isoelectric point of S100A12 is about pH 5.83; and the isoelectric point of S100A8 is about pH 6.51 whereas S100A9 has an isoelectric point of about pH 5.71. Consequently, there is a need of using a preservative anticoagulant and running buffer which pH is within the range of below pH 5.7 as a basic buffer environment will cause granulocytes, monocytes and leucocytes to release proteins and may interfere with the measurements in a lateral flow immunochromatography.

In the described preservative anticoagulant running buffer the added sugar component (glucose, dextrose, mannitol) supports the generation of ATP by glycolytic pathways. The adenine is need for synthesis of ATP whereas the citrate is needed for complexation and chelation of calcium ions and the sodium di-phosphate prevents a fall in pH. Consequently, a person skilled in the art will contemplate of adding ATP or GTP and other suitable buffer components such as malate, malonate, phosphate acetoacetate, ketoglutarate, glutaric acid, malonic acid, malic acid, and the like to achieve the described effects.

In essence, the buffer composition shall maintain optimal viability and functionality of blood cells and avoid "lesions due to blood sampling" and biochemical changes such as a further decrease in pH, build-up of lactic acid, decrease in glucose consumption, decrease in ATP level, low 2,3-DPG levels. When blood is taken, glycolysis is reduced but does not stop so that further lactate is produced which will lead to a further decrease in pH. Whole blood has a pH of about 7.20, The preservative anticoagulant solution provides buffering capability while maintaining the S100 proteins in a soluble state.

Loss of adenosine triphosphate (ATP) is associated with the cell viability. Loss of ATP causes increase in cellular rigidity and decrease in cell membrane integrity and deformability. A decrease in ATP allows the leak of Na+ and K+ through cell membrane at levels exceeding those normally seen in vivo. A fall in pH in the blood sample results in a decrease in cell 2,3-DPG level. Blood mixed in a buffer with CPDA maintains adequate levels of 2,3-DPG and no cell pathological effects are observed. Lower temperature keeps the rate of glycolysis at lower limit and is preferred but no requirement for practicing the invention.

Heparin prevents coagulation by inactivating the prophylactic activity of thrombin. The present authors did not observe any beneficial effect of using heparin in the blood sample equipment or running buffer. On the other hand, rejuvenate solutions having phosphate, inosine, glucose, pyruvate and adenine which increase the levels of 2,3-DPG and ATP in stored blood cells can be used or added. Many other factors may limit the integrity of the granulocytes, mast cells and lymphocytes in the taken blood samples. One of the important factors is also the plastic material used for the capillary material. There may be a need to coat all plastic materials to avoid lysis of blood cells and a release to the S100 proteins into the plasma portion.

Figure 3:
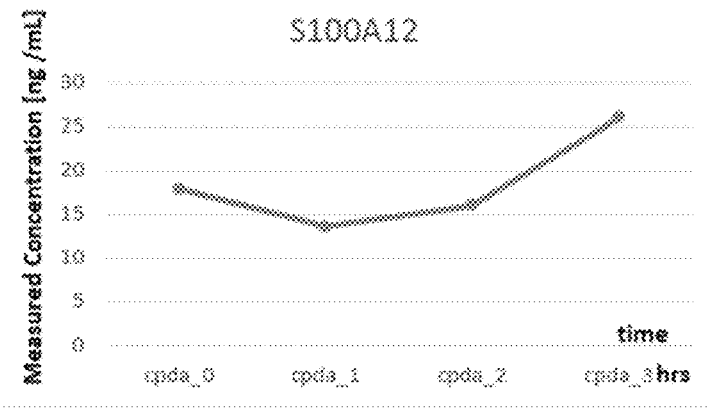
FIG. 3 is a graph wherein the abszissa values show the release of S100A12 and calprotectin from blood at room temperature when diluted in CPDA-1 buffer (citrate-phosphate-dextrose-adenine, pH 5.6)
Figure 3:
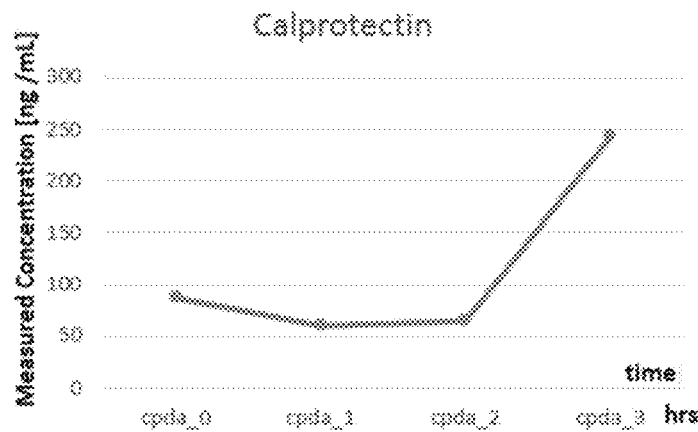

FIG. 3 demonstrates that CPDA as a representative preservative anticoagulant can be used for blood sampling without an inadvertent activation of the innate immune system. The instant disclosure shows that CPDA at pH 5.6 can be used to avoid a release of calprotectin and/or S100A12. However, these are acidic proteins with close isoelectric points. Consequently, it will be necessary to adjust the pH so that neither the antibodies nor the analytes precipitate on the chromatographic separation material. In other words, the immunochromatography must be adapted to work either in an acidified range in the range between 5.0 and 5.6 when the particulate blood components are retained on a fleece or by a microporous membrane. Alternatively, the particulate blood components must be separated from the plasma portion in a separate pre-analytical step, e.g. by gentle centrifugation at 800 g for 1 to 5 minutes. Thereafter, the plasma portion may be subjected to a pH change—diluted in another buffer—and then subjected onto the lateral flow test. Notwithstanding, a uniform sample handling without centrifugation is preferred.

Example 4 Definition of Threshold Levels of S100A12 and S100A8/A9 (Calprotectin) in Serum Capillary blood was taken from healthy and diseased subjects for measurement of the concentrations of S100A12 and S100A8/A9. 50 μl blood was added to 450 μl preservative buffer (dilution 1:10) followed by a removal of the particular blood components at 800 g for 1 minute. 50 μl supematant was then further diluted with respective ELISA sample buffer for S100A12 (Immundiagnostik AG, Bensheim, DE—article no. K6939) and calprotectin/S100A8/A9 complex (Immundiagnostik AG, Bensheim, DE—article no. K6935). The measurements were the performed as described by the manufacturer to determine the thresholds for the respective lateral flow immunoassays.

Figure 4:
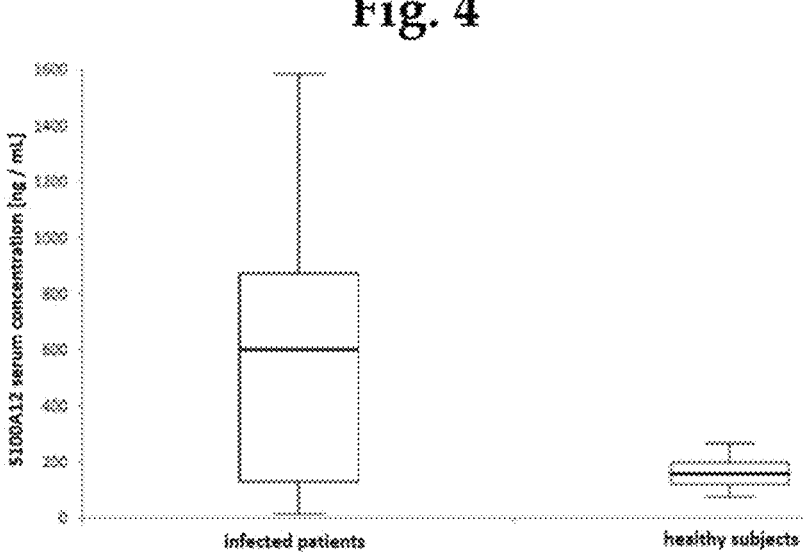
FIG. 4 is a plot comparing the S100A12 concentration in blood samples of healthy and diseased subjects as determined by a ELISA.
Figure 5:
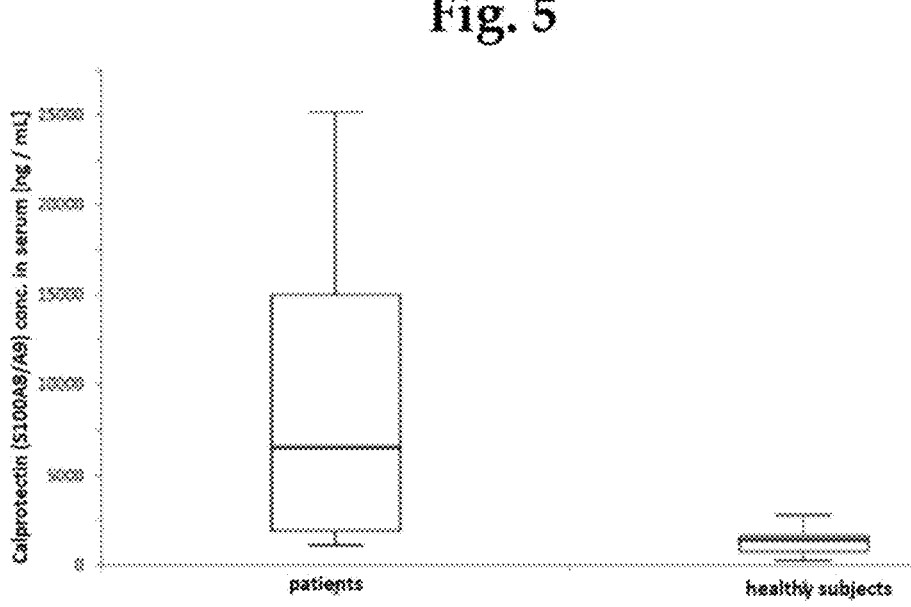
FIG. 5 is a plot comparing the calprotectin (S100A8/A9) concentration in the blood of healthy and diseased subjects as determined by a conventional ELISA.

The results are shown in Table 1 and 2 below as well as in FIGS. 4 and 5. The results show that diseased subjects can be distinguished from healthy subjects on basis of the calcium-binding S100 proteins released by neutrophil granulocytes and calprotectin primarily released of mast cells. Thus, the S100 proteins of the congenital innate immune system can be used as well in newborns and preterm infants to detect a bacterial invasion in the bloodstream as well as to differentiate this anti-microbial reaction from an inflammatory reaction which does not require a treatment with antibiotics.

Moreover, the examples show that threshold levels for S100A12 and calprotectin in serum can be established for preterm and newly born patients which can be used for a commercial test kit and a positive evaluation of unspecific symptoms which may indicate a bacterial invasion. This test can be therefore used to avoid a superfluous prophylactic antibiotics treatment of premature and newly born babies and reduce the evolvement of multi-resistant bacterial strains in neonatal intensive care units.

TABLE 1

Determination of S100A12 in healthy
and diseased subjects by ELISA

| Sample | ID | S100A12 concentration (ng/ml) |
|---|---|---|
| Patient | SH | 764 |
| Patient | MK | 596 |
| Patient | WD | 609 |
| Patient | WP | 362 |
| Patient | LM | 1100 |
| Patient | MG | 15 |
| Patient | WM | 854 |
| Patient | HLO | 104 |
| Patient | KD | 1587 |
| Patient | RD | 131 |
| healthy subject | 1 | 76 |
| healthy subject | 2 | 170 |
| healthy subject | 7 | 143 |
| healthy subject | | 121 |
| healthy subject | 10 | 168 |
| healthy subject | 12 | 194 |
| healthy subject | 13 | 269 |
| healthy subject | 14 | 110 |
| healthy subject | 18 | 136 |
| healthy subject | 23 | 270 |

TABLE 2

Determination of calprotectin
in serum of diseased and
healthy subjects by ELISA

| Sample | ID | Calprotectin concentration [ng/mL] |
|---|---|---|
| Patient | SH | 14700 |
| Patient | MK | 6408 |
| Patient | WD | 6651 |
| Patient | WP | 3221 |
| Patient | LM | 12700 |
| Patient | MG | 1065 |
| Patient | WM | 18100 |
| Patient | HLO | 1208 |
| Patient | KD | 25200 |
| Patient | RD | 1957 |
| healthy subject | 1 | 562 |
| healthy subject | 2 | 260 |
| healthy subject | 7 | 1516 |
| healthy subject | 9 | 768 |
| healthy subject | 10 | 1317 |
| healthy subject | 12 | 1532 |

TABLE 2-continued

Determination of calprotectin
in serum of diseased and
healthy subjects by ELISA

| Sample | ID | Calprotectin concentration [ng/mL] |
|---|---|---|
| healthy subject | 13 | 2759 |
| healthy subject | 14 | 813 |
| healthy subject | 18 | 1592 |
| healthy subject | 23 | 1812 |

The invention claimed is:

1. A method for point-of-care diagnosis and bedside stratification of and septic processes in a blood or serum sample of a neonate, comprising diluting a defined amount of sample in a defined amount of buffer having a pH between 5.0 and 5.7, which buffer does not induce an uncontrolled release of proteins from blood cells, granulocytes, monocytes, mast cells or leukocytes and allows for a quantitative flowthrough immunobinding assay of the S100 protein analytes, performing one or more flowthrough immunobinding assays at a pH between 5.0 and 5.7 for quantitative or semi-quantitative detection and measurement of at least two proteins of the S100 family of calcium-binding proteins, including at least separate and parallel quantitative or semi-quantitative determinations of S100A12 and calprotectin (S100A8/A9), each yielding an independent measurement result;

wherein the buffer comprises 20-30 g trisodium citrate, 2.0-5.0 g citric acid, 2.0-5.0 g monobasic sodium phosphate ($NaH_2PO_4$), and mixed with the blood component in a ratio of about 1:5 to 1:10.

2. The method of claim 1, comprising employing two separate flowthrough immunobinding assays in one housing adapted to produce visual zones indicating the presence and content of the analytes (T) in said sample and respective control zones (C).

3. The method of claim 1, further employing a portable processor device comprising a digital camera, a source of light and a processor configured to process digital images captured by said camera and to represent a diagnostic result.

4. The method of claim 1, further comprising the use of a blood sampling system which contains or is coated with an acidified preservative buffer of a pH between 5.0 and 5.7.

5. The method of claim 1, wherein the one or more lateral flow tests comprise a size-exclusion technique, comb, mesh, weir-type filter structure, microporous fleece or fabricated porous filter membrane for retention of particulate blood components and blood cells from the liquid portion.

6. A method of treating neonates suffering from an inflammatory reaction of unknown etiology comprising identifying neonates suffering from an inflammatory reaction of unknown etiology by mixing a predefined amount of bodily fluid, capillary blood or whole blood with a predefined amount of acidified buffer, having a pH in the range from 5.0 to 5.7 and a functional amount of blood preservative anticoagulant to form an acidified mixture;

applying predefined amounts of the acidified mixture onto the application zones of one or more lateral flow immunoassays and performing a lateral flow immunochromatography for separate and parallel determination of the presence and content of S100A12 and of cal-protectin, each yielding an independent measurement result; and evaluating the amounts of both S100A12 and calprotectin in the visual zones with the amounts present in samples taken from healthy subjects, where increased amounts of S100A12 and calprotectin are present and indicate the presence of a septic process, and treating the identified affected neonates with antibiotics.

7. The method of claim 6, wherein a photographic image of the lateral flow immunoassays is taken, and the diagnostic result is determined on basis of a digital photographic image using data of the visible zones and calibration data provided by the manufacturer.

8. The method of claim 6, comprising a quantitative or semi-quantitative determination of markers of the innate immune system activation.

9. The method of claim 6, comprising:

(a) taking a color digital image of the lateral flow immunoassay using a portable processor device comprising a digital camera, a source of light and a processor, wherein said processor is configured to process digital images captured by said camera and to represent an analytical result;

(b) analyzing digital image for the location of the region of interest of said one or more lateral flow tests and for the amounts of signal.

10. The method of claim 6 for simultaneous detection of S100A12 and calprotectin, comprising two parallel lateral flow immunoassays having in fluid communication (i) a sample pad at the proximal end for receiving the sample, followed by (ii) a size-exclusion technique, comb, mesh, weir-type filter structure, microporous fleece or fabricated porous filter membrane for retention of particulate blood components and blood cells from the liquid portion;

(iii) a conjugate pad containing mobile labeled immunoreactants which bind to the analyte, (iv) a membrane with porous separation material thereon, and (v) a water-adsorptive wicking pad at the distal end, wherein the separation membrane defines a proximal test zone containing immobilized capture molecules which bind to either analyte and a distal control zone for receiving mobile labeled immunoreactants.

11. The method of claim 1, wherein the blood or serum sample is capillary blood.

12. The method of claim 6, wherein the blood or serum sample is capillary blood.

* * * * *